(12) United States Patent
Okita

(10) Patent No.: US 11,389,052 B2
(45) Date of Patent: Jul. 19, 2022

(54) ENDOSCOPE AND STIFFNESS VARYING METHOD

(71) Applicant: OLYMPUS CORPORATION, Tokyo (JP)

(72) Inventor: Tatsuhiko Okita, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 323 days.

(21) Appl. No.: 16/597,281

(22) Filed: Oct. 9, 2019

(65) Prior Publication Data
US 2020/0037851 A1 Feb. 6, 2020

Related U.S. Application Data

(63) Continuation of application No. PCT/JP2017/015007, filed on Apr. 12, 2017.

(51) Int. Cl.
*A61B 1/005* (2006.01)
(52) U.S. Cl.
CPC .................... *A61B 1/0058* (2013.01)
(58) Field of Classification Search
CPC ............ A61B 1/00064; A61B 1/00078; A61B 1/0055; A61B 1/0058; A61M 25/0053;
(Continued)

(56) References Cited

U.S. PATENT DOCUMENTS

| 5,549,542 A * | 8/1996 | Kovalcheck ......... A61B 1/0052 600/146 |
| 8,366,606 B2 | 2/2013 | Watanabe et al. |

(Continued)

FOREIGN PATENT DOCUMENTS

| JP | 2002-355217 A | 12/2002 |
| JP | 2005-13296 A | 1/2005 |

(Continued)

OTHER PUBLICATIONS

English translation of International Preliminary Report on Patentability dated Oct. 24, 2019, together with the Written Opinion received in related International Application No. PCT/JP2017/015007.

(Continued)

*Primary Examiner* — Aaron B Fairchild
(74) *Attorney, Agent, or Firm* — Scully, Scott, Murphy & Presser, P.C.

(57) ABSTRACT

An endoscope includes a flexible member and a variable stiffness apparatus installed in the flexible member. The variable stiffness apparatus includes a first longitudinal member and a second longitudinal member movable along the first longitudinal member. The first longitudinal member includes a first high bending stiffness portion and a first low bending stiffness portion. The second longitudinal member includes a second high bending stiffness portion, a second low bending stiffness portion, and a soft member arranged in the second high bending stiffness portion and the second low bending stiffness portion. Stiffness of part of the variable stiffness apparatus in a longitudinal axis direction is varied by changing a relative position of the first and second longitudinal members.

18 Claims, 6 Drawing Sheets

(58) Field of Classification Search
CPC ........... A61M 25/0054; A61M 25/0147; F16L 11/081–83; F16L 11/10
See application file for complete search history.

(56) References Cited

U.S. PATENT DOCUMENTS

| | | | | |
|---|---|---|---|---|
| 2007/0043261 A1* | 2/2007 | Watanabe | ............ | A61B 1/0055 600/144 |
| 2010/0280449 A1* | 11/2010 | Alvarez | ............... | A61B 1/0055 604/95.04 |
| 2014/0155697 A1* | 6/2014 | Iede | ..................... | A61B 1/0057 600/139 |
| 2017/0254447 A1* | 9/2017 | Saito | ................... | A61B 1/0055 |
| 2018/0042458 A1* | 2/2018 | Araki | ................... | A61B 1/0055 |
| 2020/0257105 A1* | 8/2020 | Okita | .................. | A61B 1/0055 |

FOREIGN PATENT DOCUMENTS

| | | |
|---|---|---|
| JP | 2007-54125 A | 3/2007 |
| WO | 2016/174741 A1 | 11/2016 |

OTHER PUBLICATIONS

International Search Report dated Jun. 20, 2017 received in PCT/JP2017/015007.

\* cited by examiner

ENDOSCOPE AND STIFFNESS VARYING METHOD

CROSS-REFERENCE TO RELATED APPLICATIONS

This application is a Continuation Application of PCT Application No. PCT/JP2017/015007, filed Apr. 12, 2017, the entire contents of which are incorporated herein by reference.

BACKGROUND OF THE INVENTION

1. Field of the Invention

The present invention relates to an endoscope including a variable stiffness apparatus configured to provide a flexible member with different levels of stiffness, and a stiffness varying method.

2. Description of the Related Art

For example, International Publication No. 2016/174741 discloses a variable rigidity actuator for varying rigidity of a flexible member. The variable rigidity actuator is to be installed in the flexible member, provides the flexible member with different levels of rigidity, and is simple and durable. The variable rigidity actuator includes wirings configured to supply an electric current, inducing members configured to generate heat upon receiving the electric current supplied from the wirings, and a shape memory member configured to receive heat from the inducing members. The wirings are connected to the inducing members, respectively, and the inducing members are spaced apart from each other. The shape memory member transitions in phase from a first phase to a second phase by heat supplied from the inducing member. When the shape memory member is in the first phase, the shape memory member takes a low stiffness state. When the shape memory member is in the second phase, the shape memory member takes a high stiffness state having higher stiffness than in the low stiffness state. The variable rigidity actuator provides the flexible member with low stiffness by the shape memory member in the low stiffness state, and provides the flexible member with high stiffness by the shape memory member in the high stiffness state. The inducing members spaced apart from each another transmit heat to part of the shape memory member in the entire length of the shape memory member. Thus, the variable rigidity actuator varies the stiffness of the desired area of the flexible member, in other words, partially varies the stiffness of the flexible member.

BRIEF SUMMARY OF THE INVENTION

An endoscope according to the present invention includes a flexible member and a variable stiffness apparatus installed in the flexible member. The variable stiffness apparatus includes a first longitudinal member and a second longitudinal member movable along the first longitudinal member. The first longitudinal member includes at least one first high bending stiffness portion and at least one first low bending stiffness portion having lower bending stiffness than bending stiffness of the first high bending stiffness portion. The second longitudinal member includes at least one second high bending stiffness portion, at least one second low bending stiffness portion having lower bending stiffness than bending stiffness of the second high bending stiffness portion, and a soft member arranged in the second high bending stiffness portion and the second low bending stiffness portion. Stiffness of part of the variable stiffness apparatus in a longitudinal axis direction of the variable stiffness apparatus is varied by changing a relative position of the first longitudinal member and the second longitudinal member.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, an embodiment of the present invention will be described with reference to the drawings. In some drawings, part of the members is not shown so as to clarify the illustration.

Figure 1A:
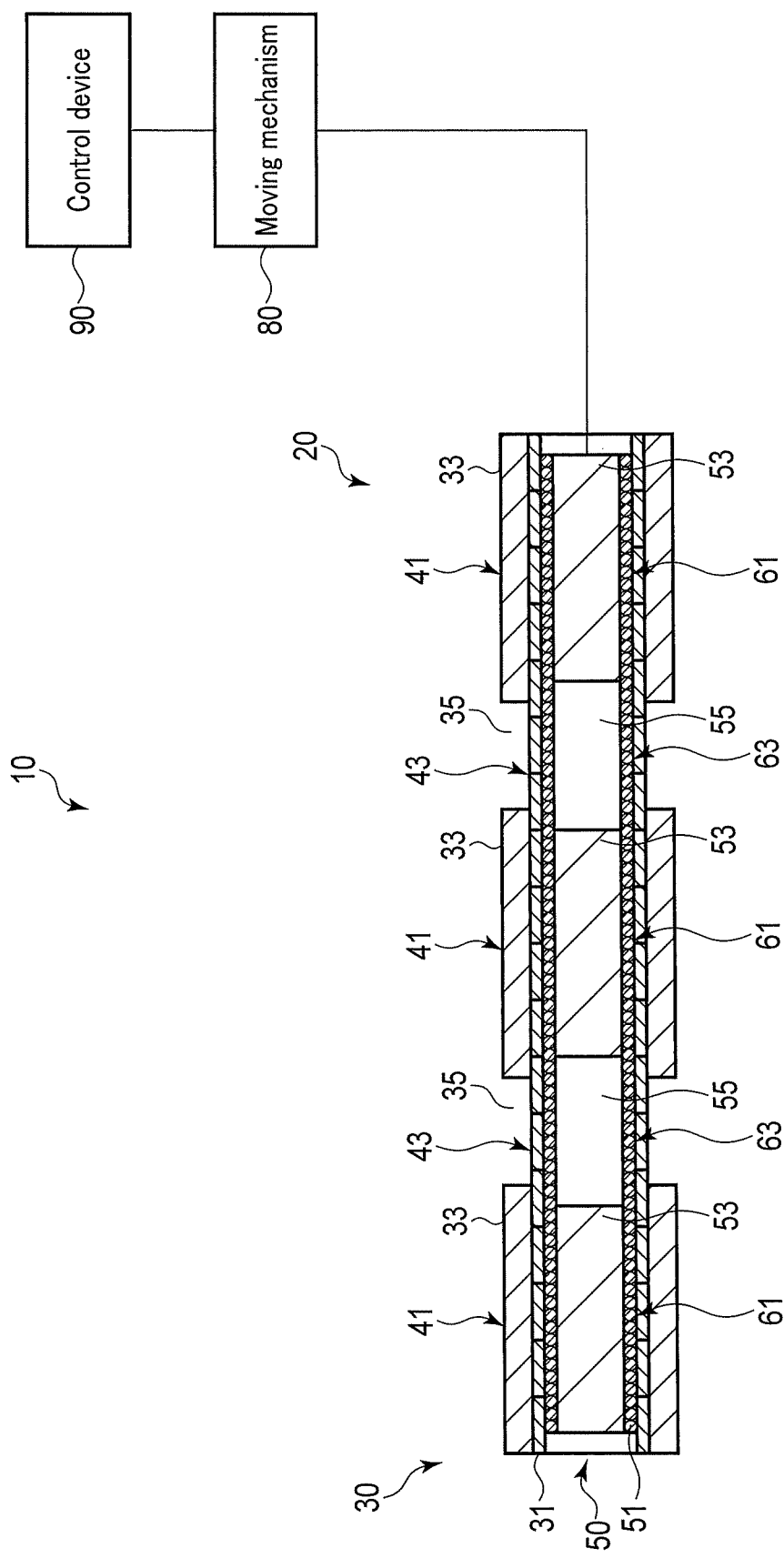
FIG. 1A is a schematic view of a variable stiffness system according to one embodiment of the present invention, showing that a variable stiffness apparatus of the variable stiffness system is in a first state.
Figure 1B:
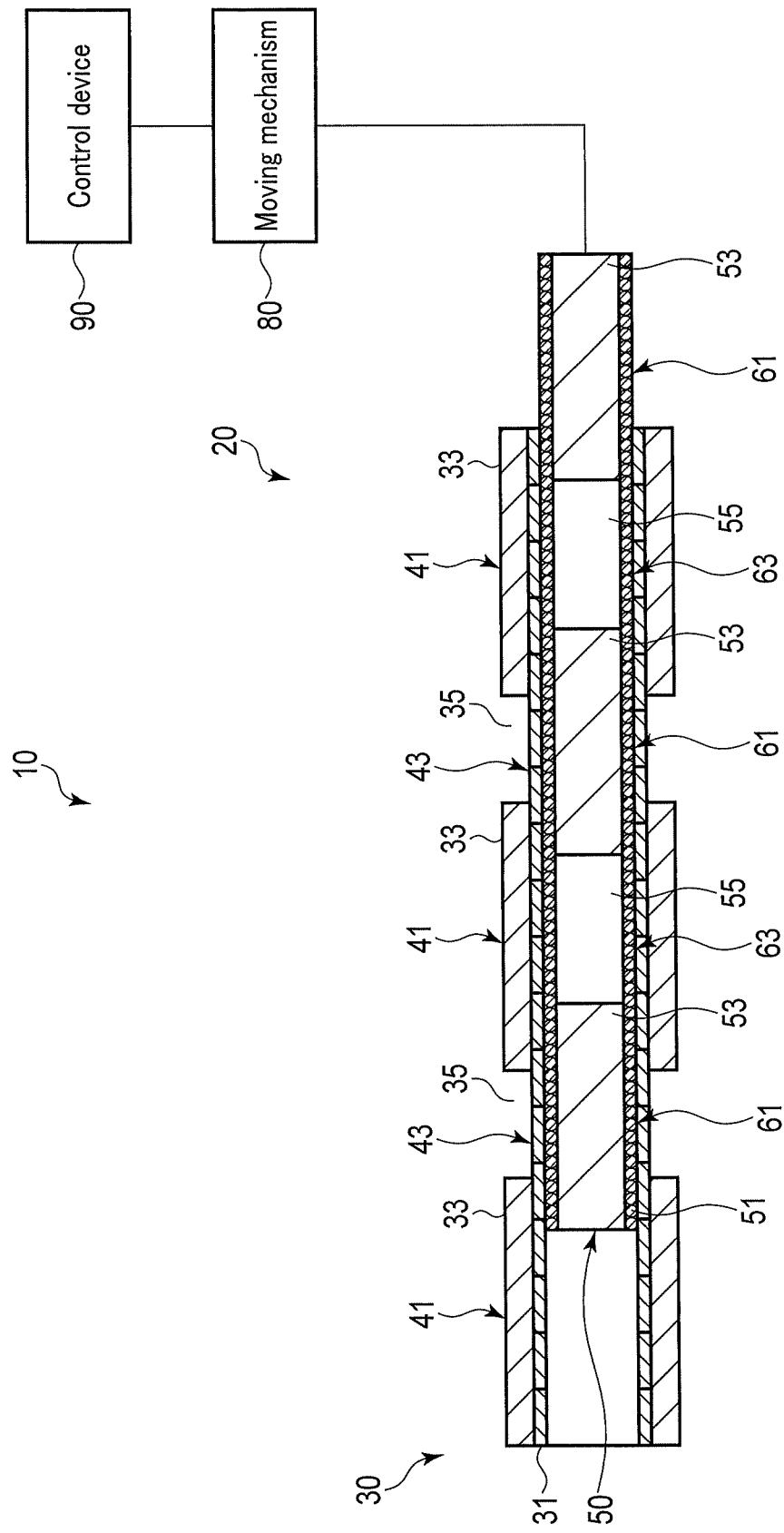
FIG. 1B is a diagram showing that the variable stiffness apparatus shown in FIG. 1A is switched to a second state.
Figure 1C:
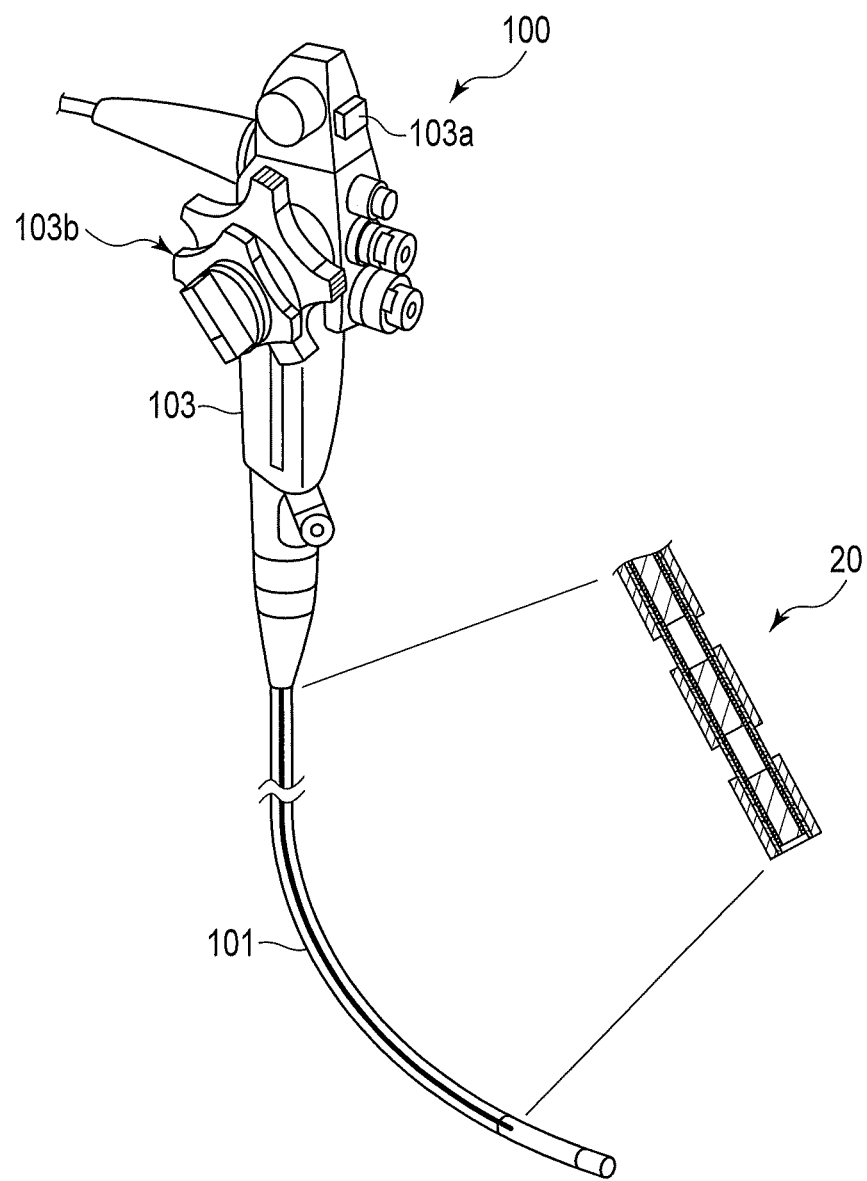
FIG. 1C is a perspective view of an endoscope in which the variable stiffness apparatus is incorporated.

As shown in FIG. 1A, FIG. 1B, and FIG. 1C, the variable stiffness system 10 includes a variable stiffness device 20 installed in the flexible member 101, for example, and a control device 90 configured to control the variable stiffness apparatus 20.

The variable stiffness apparatus 20 provides the flexible member 101 with different levels of stiffness. The variable stiffness apparatus 20 includes a first longitudinal member 30, and a second longitudinal member 50 movable along the first longitudinal member 30. The second longitudinal member 50 is next to the first longitudinal member 30. The second longitudinal member 50 may adjacent to the first longitudinal member 30. For example, the first longitudinal member 30 is an outer cylinder, and the second longitudinal member 50 is a core member arranged inside the first longitudinal member 30. For example, the cross-sectional shape of the outer cylinder perpendicular to the longitudinal axis of the outer cylinder is annular shape, and the outer periphery of the cross section of the core member perpendicular to the longitudinal axis of the core member is annular shape. In this case, the variable stiffness apparatus 20 provides bends in any direction with stable stiffness. The cross-sectional shape of each of the outer cylinder and the core member needs not necessarily be an annular shape, and may be another shape; for example, a C-shape. In the present embodiment, for example, the first longitudinal member 30 is positioned and fixed relative to the flexible member 101. For example, the second longitudinal member 50 is movable relative to the first longitudinal member 30 and the flexible member 101.

The first longitudinal member 30 includes a tubular core member 31 into which the second longitudinal member 50 is inserted, and at least one tubular first rigid member 33 arranged on the outer periphery of the core member 31.

The core member 31 covers the second longitudinal member 50 over the entire length of the second longitudinal member 50. For example, the length of the core member 31 is longer than the length of the second longitudinal member 50. The length of the core member 31 may be about the same as the length of the second longitudinal member 50. The core member 31 is arranged over the entire length of the variable stiffness apparatus 20. The core member 31 is inserted into the first rigid member 33, and is arranged inside the first rigid member 33. For example, the core member 31 functions as a core for the first rigid member 33. The core member 31 is a tubular support member supporting the first rigid member 33.

The core member 31 has, for example, a spiral coil member such as a tightly-wound coil. The coil member of the core member 31 may be a loosely-wound coil. The core member 31 may have, for example, a wire-like and spiral member of metal. The core member 31 is a hollow member; for example, cylindrical.

In the present embodiment, assume that three first rigid members 33 are arranged. The first rigid member 33 is a hollow member; for example, cylindrical. The first rigid member 33 has, for example, a metal pipe. The first rigid member 33 is a separate member from the core member 31. The first rigid member 33 is shorter than the core member 31.

The inner peripheral surface of the first rigid member 33 is fixed to the outer peripheral surface of the core member 31 by, for example, bonding or welding. The first rigid member 33 is positioned on the core member 31 so that the first rigid member 33 surrounds the core member 31. The first rigid members 33 are not in direct mechanical contact with each other in the longitudinal direction of the first longitudinal member 30, but are arranged at desired intervals with respect to each other. That is, the first rigid members 33 partially surround the core member 31 over the entire length of the core member 31. That is, one first rigid member 33 does not surround the core member 31 over the entire length of the core member 31, but surrounds part of the core member 31 in the entire length of the core member 31. Therefore, a first space 35 is arranged between the first rigid members 33 in the longitudinal direction of the first longitudinal member 30. In the present embodiment, assume that two first spaces 35 are arranged. No member is arranged in the first space 35. The length of the first rigid member 33 is different from the length of the first space 35; for example, longer than the length of the first space 35. The length of the first rigid member 33 may be about the same as the length of the first space 35. In the first space 35, the outer peripheral surface of the core member 31 is exposed to the outside of the first longitudinal member 30. The first space 35 indicates part of the core member 31 that is not covered with the first rigid member 33 in the entire length of the core member 31. Since the first longitudinal member 30 is positioned and fixed relative to the flexible member 101, the first space 35 is positioned and fixed relative to the desired area of the flexible member 101. The longitudinal axis direction of the first longitudinal member 30 is the horizontal direction in FIG. 1A.

The first rigid members 33 and the first spaces 35 are alternately arranged on the outer peripheral surface of the core member 31 in the longitudinal axis direction of the first longitudinal members 30. The number of the first rigid members 33 and the number of the first spaces 35 are not particularly limited as long as the first rigid members 33 and the first spaces 35 are alternately arranged. It suffices if at least one first rigid member 33 and at least one first space 35 are arranged.

The first longitudinal member 30 includes at least one first high bending stiffness portion 41 having relatively high bending stiffness and at least one first low bending stiffness portion 43 having relatively low bending stiffness. That is, the bending stiffness of the first high bending stiffness portion 41 is high, and the bending stiffness of the first low bending stiffness portion 43 is lower than the bending stiffness of the first high bending stiffness portion 41. In the present embodiment, for example, assume the first longitudinal member 30 includes three first high bending stiffness portions 41 and two first low bending stiffness portions 43.

The first high bending stiffness portion 41 includes, for example, the tubular first rigid member 33 covering the core member 31. The first high bending stiffness portion 41 further includes part of the core member 31 covered with the first rigid member 33. That is, the first high bending stiffness portion 41 includes the first rigid member 33 and part of the core member 31 on the periphery of the first rigid member 33.

The first low bending stiffness portion 43 has part of the core member 31 not covered with the first rigid member 33. In other words, the first low bending stiffness portion 43 has part of the core member 31 in the first space 35.

The core member 31 is arranged in the first high bending stiffness portions 41 and the first low bending stiffness portions 43, and the core member 31 is shared by the first high bending stiffness portions 41 and the first low bending stiffness portions 43.

In the first high bending stiffness portion 41, the outer peripheral surface of the first rigid member 33 is exposed to the outside of the first longitudinal member 30. In the first low bending stiffness portion 43, the outer peripheral surface of the core member 31 is exposed to the outside of the first longitudinal member 30. In the first low bending stiffness portion 43, the core member 31 is exposed to the outside from the first rigid member 33, and protrudes to the outside with respect to the first rigid member 33.

The core member 31 is a tubular soft portion having low bending stiffness, and the first rigid member 33 is a tubular rigid portion having high bending stiffness. Bending stiffness of the core member 31 may be about the same as the bending stiffness of the first rigid member 33. Therefore, the bending stiffness of the first high bending stiffness portion 41 including both the core member 31 and the first rigid member 33 is high, and the bending stiffness of the first low bending stiffness portion 43 including only the core member 31 is low. The first longitudinal member 30 is relatively difficult to bend at the first high bending stiffness portion 41, and the first longitudinal member 30 is relatively easy to bend at the first low bending stiffness portion 43.

The first high bending stiffness portions 41 and the first low bending stiffness portions 43 are arranged along the longitudinal axis direction of the first longitudinal member 30.

The first rigid members 33 and the first spaces 35 are alternately arranged. By this arrangement, the first high bending stiffness portions 41 and the first low bending stiffness portions 43 are alternately arranged in the longitudinal axis direction of the first longitudinal member 30. As long as the first high bending stiffness portions 41 and the first low stiffness portions 43 are alternately arranged, the number of the first high bending stiffness portions 41 and the number of the first low bending stiffness portions 43 are not particularly limited. Depending on the length of the first rigid member 33 and the length of the first space 35, the length of the first high bending stiffness portion 41 is longer than or about the same as the length of the first low bending stiffness portion 43.

The core member 31 is arranged, for example, for positioning the first rigid members 33, and defining the intervals (the length of the first spaces 35) between the first rigid members 33. The core member 31 is arranged, for example, for positioning the first high bending stiffness portions 41 and the first low bending stiffness portions 43, and defining respective lengths of the first high bending stiffness portions 41 and the first low bending stiffness portions 43. The core member 31 is arranged for assembling the first longitudinal member 30.

First high bending stiffness portions 41 (first rigid members 33) are arranged at the both ends of the first longitudinal member 30; however, the arrangement does not need to be limited thereto. First low bending stiffness portions 43 may be arranged at the both ends, or it may be that a first high bending stiffness portion 41 (a first rigid member 33) is arranged at an end and a first low bending stiffness portion 43 is arranged at the other end.

The second longitudinal member 50 is arranged inside the core member 31. The outer peripheral surface of the second longitudinal member 50 (a soft member 51 described later) is not in contact with the inner peripheral surface of the core member 31, and a space is formed between the core member 31 and the second longitudinal member 50. The outer peripheral surface may be in contact with the inner peripheral surface.

The second longitudinal member 50 includes a soft member 51 and at least one second rigid member 53. The soft member 51 is inserted into the core member 31, and tubular. The second rigid member 53 is arranged inside the soft member 51.

The soft member 51 inserted into the core member 31 is covered with the core member 31 over the entire length of the soft member 51. For example, the length of the soft member 51 is shorter than the length of the core member 31. The length of the soft member 51 may be about the same as the length of the core member 31. The soft member 51 is arranged over the entire length of the variable stiffness apparatus 20. The second rigid member 53 is inserted into the soft member 51, and the soft member 51 is arranged outside the second rigid member 53. The soft member 51 functions as a protective member configured to protect the outer peripheral surface of the second rigid member 53 from the inner peripheral surface of the core member 31. The soft member 51 is an intervening member that is interposed between the core member 31 and the second rigid member 53, and that prevents the second rigid member 53 from being in direct contact with the core member 31. The soft member 51 is a tubular support member supporting the second rigid member 53.

Figure 2A:
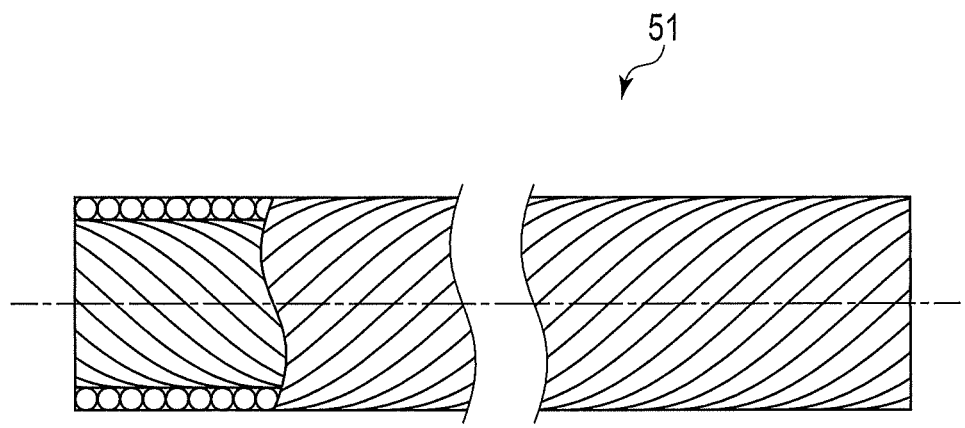
FIG. 2A is a diagram showing an example of a soft member of the variable stiffness apparatus.
Figure 2B:
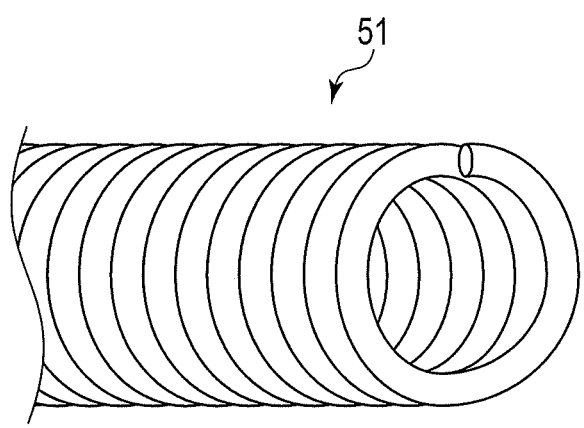
FIG. 2B is a diagram showing an example of the soft member of the variable stiffness apparatus.

The soft member 51 may have, for example, a metal member. As shown in FIG. 2A, the soft member 51 may have, for example, a twisted wire sleeve in which metal wires are twisted with each other. As shown in FIG. 2B, the soft member 51 may have, for example, a contact coil. The soft member 51 may have a loosely-wound coil. The soft member 51 may have a resin material. The soft member 51 is a hollow member; for example, cylindrical.

In the present embodiment, assume that three second rigid members 53 are arranged. The second rigid member 53 may be, for example, a solid member or a hollow member. The second rigid member 53 may be of, for example, a metal material or a resin material. The second rigid member 53 is a separate member from the soft member 51. The second rigid member 53 is shorter than the soft member 51.

The inner peripheral surface of the soft member 51 is fixed to the outer peripheral surface of the second rigid member 53 by, for example, bonding or welding. The second rigid members 53 are positioned on the soft member 51 so that the second rigid members 53 are arranged inside the soft member 51. The second rigid members 53 are not in direct mechanical contact with each other in the longitudinal direction of the second longitudinal member 50, but are arranged at desired intervals with respect to each other. That is, the second rigid members 53 are partially arranged inside the soft member 51 over the entire length of the soft member 51. That is, one second rigid member 53 is not arranged inside the soft member 51 over the entire length of the soft member 51, but is arranged in part of the soft member 51 in the entire length of the soft member 51. Therefore, second spaces 55 are arranged between the second rigid members 53 in the longitudinal direction of the second longitudinal member 50. In the present embodiment, assume that two second spaces 55 are arranged. No member is arranged in the second space 55. The length of the second rigid member 53 is different from the length of the second space 55; for example, longer than the length of the second space 55. The length of the second rigid member 53 may be about the same as the length of the second space 55. The second spaces 55 indicate part of the soft member 51 where the second rigid member 53 is not arranged in the entire length of the core member 51. The longitudinal axis direction of the second longitudinal member 50 is the horizontal direction in FIG. 1A, and is the same direction as the longitudinal axis direction of the first longitudinal member 30.

The second rigid members 53 and the second spaces 55 are alternately arranged inside the soft member 51 in the longitudinal axis direction of the second longitudinal member 50. As long as the second rigid members 53 and the second spaces 55 are alternately arranged, the number of the second rigid members 53 and the number of the second spaces 55 are not particularly limited. It suffices if at least one second rigid member 53 and at least one second space 55 are arranged.

The second longitudinal member 50 includes at least one second high bending stiffness portion 61 having relatively high bending stiffness and at least one second low bending stiffness portion 63 having relatively low bending stiffness. That is, the bending stiffness of the second high bending stiffness portion 61 is high, and the bending stiffness of the second low bending stiffness portion 63 is lower than the bending stiffness of the second high bending stiffness portion 61. In the present embodiment, for example, assume that the second longitudinal member 50 includes three second high bending stiffness portions 61 and two second low bending stiffness portions 63.

The second high bending stiffness portion 61 includes, for example, the second rigid member 53 arranged inside the soft member 51. The second high bending stiffness portion 61 further includes part of the soft member 51 covering the second rigid member 53. That is, the second high bending stiffness portion 61 includes the second rigid member 53 and part of the soft member 51 on the periphery of the second rigid member 53.

The second low bending stiffness portion 63 has part of the soft member 51 covering an inner space of the soft member 51 where the second rigid members 53 are not arranged inside the soft member 51. In other words, the second low bending stiffness portion 63 has part of the soft member 51 in the second space 55.

The soft member 51 is arranged in the second high bending stiffness portions 61 and the second low bending stiffness portions 63, and the soft member 51 is shared by the second high bending stiffness portions 61 and the second low bending stiffness portions 63.

The soft member 51 is a tubular soft portion having low bending stiffness, and the second rigid member 53 is a rigid portion having high bending stiffness. Bending stiffness of the soft member 51 may be about the same as bending stiffness of the second rigid member 53. Therefore, the bending stiffness of the second high bending stiffness portion 61 including both the soft member 51 and the second rigid member 53 is high, and the bending stiffness of the second low bending stiffness portion 63 including only the soft member 51 is low. The second longitudinal member 50 is relatively difficult to bend at the second high bending stiffness portion 61, and the second longitudinal member 50 is relatively easy to bend at the second low bending stiffness portion 63.

The second high bending stiffness portions 61 and the second low bending stiffness portions 63 are arranged along the longitudinal axis direction of the second longitudinal member 50.

The second rigid members 53 and the second spaces 55 are alternately arranged. By this arrangement, the second high bending stiffness portions 61 and the second low bending stiffness portions 63 are alternately arranged in the longitudinal axis direction of the second longitudinal member 50. As long as the second high bending stiffness portions 61 and the second low stiffness portions 63 are alternately arranged, the number of the second high bending stiffness portions 61 and the number of the second low bending stiffness portions 63 are not particularly limited. Depending on the length of the second rigid member 53 and the length of the second space 55, the length of the second high bending stiffness portion 61 is longer than or about the same as the length of the second low bending stiffness portion 63.

The soft member 51 is arranged, for example, for positioning the second rigid members 53, and defining the intervals (the length of the second space 55) between the second rigid members 53. The soft member 51 is arranged, for example, for positioning the second high bending stiffness portions 61 and the second low bending stiffness portions 63, and defining respective lengths of the second high bending stiffness portions 61 and the second low bending stiffness portions 63. The soft member 51 is arranged for assembling the second longitudinal member 50.

Second high bending stiffness portions 61 (second rigid members 53) are arranged at the both ends of the second longitudinal member 50; however, the arrangement does not need to be limited thereto. Second low bending stiffness portions 63 may be arranged at the both ends, or it may be that a second high bending stiffness portion 61 is arranged at an end and a second low bending stiffness portion 63 is arranged at the other end.

For example, the length of the second rigid member 53 is longer than the length of the first space 35. Therefore, the length of the second high bending stiffness portion 61 is longer than the length of the first low bending stiffness portion 43.

For example, the bending stiffness of the second rigid member 53 is about the same as the bending stiffness of the first rigid member 33. Therefore, the bending stiffness of the second high bending stiffness portion 61 is about the same as the bending stiffness of the first high bending stiffness portion 41.

The bending stiffness of the second rigid member 53 may be higher or lower than the bending stiffness of the first rigid member 33. Therefore, the bending stiffness of the second high bending stiffness portion 61 may be higher or lower than the bending stiffness of the first high bending stiffness portion 41.

For example, the bending stiffness of the soft member 51 is about the same as the bending stiffness of the core member 31. Therefore, the bending stiffness of the second low bending stiffness portion 63 is about the same as the bending stiffness of the first low bending stiffness portion 43.

As long as the bending stiffness of the core member 31 and the bending stiffness of the soft member 51 are respectively lower than the bending stiffness of the first rigid member 33 and the bending stiffness of the second rigid member 53, the bending stiffness of the soft member 51 may be higher or lower than the bending stiffness of the core member 31. Further, as long as the bending stiffness of the first low bending stiffness portion 43 and the bending stiffness of the second low bending stiffness portion 63 are respectively lower than the bending stiffness of the first high bending stiffness portion 41 and the bending stiffness of the second high bending stiffness portion 61, the bending stiffness of the second low bending stiffness portion 63 may be higher or lower than the bending stiffness of the first low bending stiffness portion 43.

Changing the relative position of the first longitudinal member 30 and the second longitudinal member 50 causes variation in the stiffness of part of the variable stiffness apparatus 20 in the longitudinal axis direction of the variable stiffness apparatus 20 in the horizontal direction of FIG. 1A. Thereby, the variable stiffness apparatus 20 provides the flexible member 101 with different levels of stiffness. For this purpose, for example, the variable stiffness apparatus 20 includes a moving mechanism 80 configured to move the second longitudinal member 50 relative to the first longitudinal member 30. In the present embodiment, the moving mechanism 80 allows the second longitudinal member 50 to move along the first longitudinal member 30. The outer peripheral surface of the soft member 51 slides on the inner peripheral surface of the core member 31. The moving mechanism 80 moves the second longitudinal member 50 by pulling or pushing the second longitudinal member 50. For example, the soft member 51 is pulled or pushed. In accordance with the movement of the second longitudinal member 50, the second rigid members 53, the second high bending stiffness portions 61, and the second low bending stiffness portions 63 also move. The moving mechanism 80 is electrically connected to the control device 90, and the movement is controlled by the control device 90.

The moving mechanism 80 includes, for example, a motor (not shown), and a moving member (not shown) that is connected to one end of the second longitudinal member 50 and configured to move the second longitudinal member 50 by a rotational force of the motor. The motor may be arranged in the control section 103 (see FIG. 1C) coupled to the proximal end of the insertion section (described later) that functions as the flexible member 101. The motor may be driven by an operation such as ON or OFF of the switch 103*a* at the control section 103. The moving member is, for example, directly connected to one end of the soft member 51, and pulls or pushes the second longitudinal member 50 by a rotational force. The moving member is arranged from the arrangement position of the motor to the one end of the soft member 51. For example, the moving member is arranged inside the control section 103 and the flexible member 101. The moving member is, for example, a wire-like member.

In the moving mechanism 80, a motor may be omitted, and the second longitudinal member 50 may be moved by a manual operation. For example, the moving mechanism 80 may have a control dial 103*b* in place of the motor. The control dial 103*b* is arranged on the control section 103, and is connected to the moving member. For example, the control dial 103*b* is operated by a finger of a hand gripping the control section 103, and rotated about the central axis of the control dial 103*b* by the operation. The control dial 103*b* is switched between the ON position and the OFF position by rotation. In response to the switching, the moving member is pulled or pushed. Thereby, the second longitudinal member 50 moves. Instead of the control dial 103*b*, a lever (not shown) may be used.

The control device 90 is constituted by, for example, a hardware circuit including an ASIC, etc. The control device 90 may be constituted by a processor. If the control device 90 is constituted by a processor, a program code for causing the processor to function as the control device 90 by executing the program code is stored in an internal memory of the processor or in an external memory (not shown) arranged to be accessible by the processor. The control device 90 may be arranged in the control section 103, for example. The control device 90 controls the pulling, pushing, and stopping of the moving mechanism 80 in in conjunction with the operation of the switch 103*a*.

By moving the second longitudinal member 50, the variable stiffness apparatus 20 switches a positional state of the second longitudinal member 50 relative to the first longitudinal member 30 between a first state to provide the flexible member 101 with first stiffness and a second state to provide the flexible member 101 with second stiffness higher than the first stiffness.

In the first state shown in FIG. 1A, the second high bending stiffness portion 61 is arranged on the periphery of the first high bending stiffness portion 41, and the second low bending stiffness portion 63 is arranged on the periphery of the first low bending stiffness portion 43. The periphery of the first high bending stiffness portion 41 in the first state means a position where the second high bending stiffness portion 61 is adjacent to the first high bending stiffness portion 41. In detail, this periphery means a position where the second high bending stiffness portion 61 overlaps the first high bending stiffness portion 41 over the entire length of the second high bending stiffness portion 61. That is, the second high bending stiffness portion 61 is covered with the first high bending stiffness portion 41, and is contained in the first high bending stiffness portion 41. The periphery of the first low bending stiffness portion 43 in the first state means a position where the second low bending stiffness portion 63 is adjacent to the first low bending stiffness portion 43. In detail, this periphery means a position where the first low bending stiffness portion 43 overlaps the second low bending stiffness portion 63 over the entire length of the first low bending stiffness portion 43. That is, a large of the second low bending stiffness portion 63 is covered with the first low bending stiffness portion 43, and is contained in the first low bending stiffness portion 43. In this manner, in the first state, the second high bending stiffness portion 61 is arranged inside the first high bending stiffness portion 41, and the first low bending stiffness portion 43 is arranged around the second low bending stiffness portion 63.

The first high bending stiffness portions 41 and the first low bending stiffness portions 43 are alternately arranged, and the second high bending stiffness portions 61 and the second low bending stiffness portions 63 are alternately arranged. Therefore, in the first state, the second low bending stiffness portion 63 contained in the first low bending stiffness portion 43 is arranged next to the second high bending stiffness portion 61 contained in the first high bending stiffness portion 41. In the first state, since the soft first low bending stiffness portion 43 overlaps the soft second low bending stiffness portion 63, the first low bending stiffness portion 43 is in such a state that it is easy to bend.

In the first state, the first longitudinal member 30 and the second longitudinal member 50 are in a low stiffness state where they can be easily deformed according to an external force. Thus, in the first state, the variable stiffness apparatus 20 provides the flexible member 101 with a relatively low stiffness such that the flexible member 101 is easily bent. In the first state, the first longitudinal member 30, the second longitudinal member 50, and the flexible member 101 can be easily bent, for example, by an external force.

In the second state shown in FIG. 1B, the second high bending stiffness portion 61 is arranged on the periphery of the first low bending stiffness portion 43, and the second low bending stiffness portion 63 is arranged on the periphery of the first high bending stiffness portion 41. The periphery of the first low bending stiffness portion 43 in the second state means a position where the first low bending stiffness portion 43 is adjacent to the second high bending stiffness portion 61. In detail, this periphery means a position where the first low bending stiffness portion 43 overlaps the second high bending stiffness portion 61 over the entire length of the first low bending stiffness portion 43. That is, the first low bending stiffness portion 43 covers a large part of the second high bending stiffness portion 61, and contains the large part of the second high bending stiffness portion 61. The periphery of the first high bending stiffness portion 41 in the second state means a position where the second low bending stiffness portion 63 is adjacent to the first high bending stiffness portion 41. In detail, this periphery means a position where the second low bending stiffness portion 63 overlaps the first high bending stiffness portion 41 over the entire length of the second low bending stiffness portion 63. That is, the second low bending stiffness portion 63 is covered with the first high bending stiffness portion 41, and is contained in the first high bending stiffness portion 41. In this manner, in the second state, the second low bending stiffness portion 63 is arranged inside the first high bending stiffness portion 41, and the first low bending stiffness portion 43 is arranged around the second high bending stiffness portion 61.

The first high bending stiffness portions 41 and the first low bending stiffness portions 43 are alternately arranged, and the second high bending stiffness portions 61 and the second low bending stiffness portions 63 are alternately arranged. Therefore, in the second state, the second high bending stiffness portion 61 contained in the first low bending stiffness portion 43 is arranged next to the second low bending stiffness portion 63 contained in the first high bending stiffness portion 41. In the second state, since the soft first low bending stiffness portion 43 overlaps the hard second high bending stiffness portion 61, the first low bending stiffness portion 43 is in such a state that it is difficult to bend.

In the second state, the first longitudinal member 30 and the second longitudinal member 50 are in the high stiffness state having stiffness higher than in the low stiffness state. Therefore, in the second state, the variable stiffness apparatus 20 takes a high stiffness state with a tendency in which the flexible member 101 has a shape that is difficult to be bent against an external force, so as to provide the flexible member 101 with relatively high stiffness such that the flexible member 101 is difficult to be bent. The shape that is difficult to be bent may be, for example, linear. In the second state, the first longitudinal member 30, the second longitudinal member 50, and the flexible member 101 can maintain an approximately linear state, or can be more gently bent by an external force than in the first state, for example.

Here, the external force means a force capable of deforming the first longitudinal member 30 and the second longitudinal member 50, and gravity is also considered as part of the external force.

Herein, the relationship between the variable stiffness apparatus 20 and the flexible member 101 will be described.

The variable stiffness apparatus 20 is installed in the flexible member 101 without any restriction on the second longitudinal member 50 and the moving member. For example, the first longitudinal member 30, the second longitudinal member 50, and the moving member are arranged with a small space in a limited space of the flexible member 101. The limited space means a space that can just contain the first longitudinal member 30, the second longitudinal member 50, and the moving member. Accordingly, even if deformation of either the first longitudinal member 30 and the second longitudinal member 50 or the flexible member 101 is slight, either one of them may come into contact with the other to give an external force to the other. The flexible member 101 only needs to have a space slightly larger than the first longitudinal member 30, the second longitudinal member 50, and the moving member.

For example, the flexible member 101 is a tube having an inner diameter slightly larger than the outer diameter of the variable stiffness apparatus 20, particularly the outer diameter of the first rigid member 33, and able to be bent by the application of an external force. The first longitudinal member 30, the second longitudinal member 50, and the moving member may be arranged inside the tube. The first longitudinal member 30 is positioned and fixed relative to the flexible member 101, and the second longitudinal member 50 is movable relative to the first longitudinal member 30 and the flexible member 101. The flexible member 101 may be, for example, an insertion section of an endoscope 100. The endoscope 100 may be for a medical purpose or an industrial purpose. Thus, as shown in FIG. 1C, the endoscope 100 comprises a flexible member 101 and a variable stiffness apparatus 20 that is installed in the flexible member 101 and configured to provide the flexible member 101 with different levels of stiffness. The flexible member 101 is an example of a small-sized precision device in which the variable stiffness apparatus 20 is installed. Examples of this small-sized precision device include, for example, a manipulator and an elongated member such as a catheter, in addition to an insertion section. The motor of the moving mechanism 80 and control device 90 may be arranged in the endoscope 100, or may be arranged in a control device (not shown) for the endoscope 100 connected to the endoscope 100. Therefore, the variable stiffness system 10 is arranged in the endoscope 100, or is arranged in the endoscope system including the endoscope 100 and the control device for the endoscope 100.

Hereinafter, the variation of the stiffness of the desired area in the flexible member 101 in the present embodiment will be described.

First, as shown in FIG. 1A, assume that the variable stiffness system 10 is in a first state that is an initial state. In the initial state, the moving mechanism 80 is not driven, and the first longitudinal member 30 and the second longitudinal member 50 are in a low stiffness state over the entire length.

If the switch 103a in the control section 103 is turned on, the control device 90 controls the moving mechanism 80 so that the positional state switches from the first state to the second state.

As shown in FIG. 1B, the moving mechanism 80 moves the second longitudinal member 50 relative to the first longitudinal member 30, so that the positional state switches from the first state to the second state. At this time, the first low bending stiffness portion 43 overlaps the second high bending stiffness portion 61 over the entire length of the first low bending stiffness portion 43, and the second low bending stiffness portion 63 overlaps the first high bending stiffness portion 41 over the entire length of the second low bending stiffness portion 63. The variable stiffness apparatus 20 takes a high stiffness state in the first low bending stiffness portion 43. That is, the stiffness of the variable stiffness apparatus 20 partially increases in the longitudinal axis direction of the variable stiffness apparatus 20.

The first space 35 (first low bending stiffness portion 43) is positioned and fixed relative to the desired area of the flexible member 101. Thus, by the second high bending stiffness portion 61 overlapping the first low bending stiffness portion 43, relatively high stiffness is provided to the desired area to which the first low bending stiffness portion 43 is fixed, which leads to increase in stiffness of the desired area. That is, the stiffness increases in part of the flexible member 101 where the first low bending stiffness portion 43 that the second high bending stiffness portion 61 overlaps is arranged. In other words, the variable stiffness apparatus 20 provides high stiffness to only part of the flexible member 101 over the entire length of the flexible member 101. Therefore, the flexible member 101 does not switch from the low stiffness state to the high stiffness state over the entire length of the flexible member 101, but partially switches from the low stiffness state to the high stiffness state. In other words, part of the total length of the flexible member 101 switches from the low stiffness state to the high stiffness state. Thus, the variable stiffness apparatus 20 varies the stiffness state of the variable stiffness apparatus 20 on the periphery of the first low bending stiffness portion 43, which results in a variation in the stiffness of the desired area in the flexible member 101. In the present embodiment, two first low bending stiffness portions 43 are arranged. Thus, the number of parts and the number of desired areas are two. The number of the parts and the number of the desired areas correspond to the number of the first low bending stiffness portions 43.

Part of the flexible member 101 in the high stiffness state counteracts an external force acting on the flexible member 101, namely, a force that may deform the second high bending stiffness portion 61. Therefore, part of the flexible member 101 in the high stiffness state maintains an approximately linear state.

The first high bending stiffness portions 41 and the second high bending stiffness portions 61 are continuously and alternately arranged in the longitudinal axis direction of the variable stiffness apparatus 20. As a result, the variable stiffness apparatus 20 takes a high stiffness state over the entire length, so as to provide high stiffness over the entire length of the flexible member 101. Furthermore, the flexible member 101 maintains an approximately linear state over the entire length.

Figure 3A:
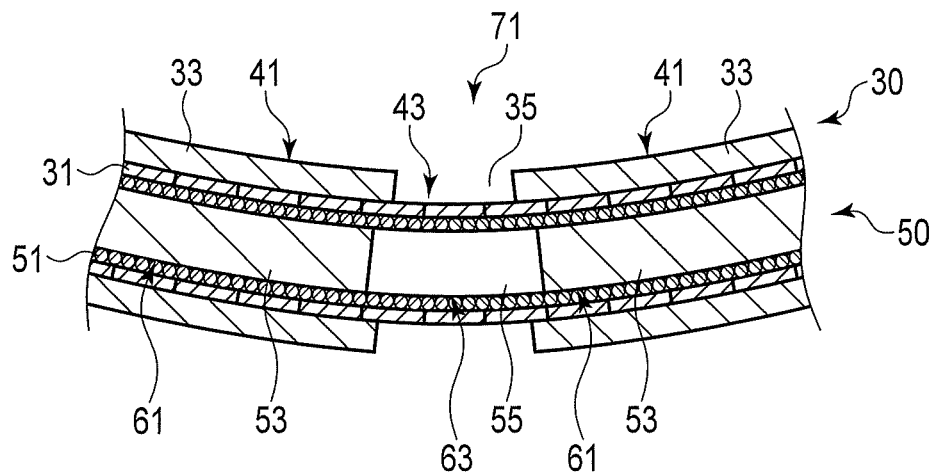
FIG. 3A is a diagram showing that a joint of the variable stiffness apparatus is in a low stiffness state.
Figure 3B:
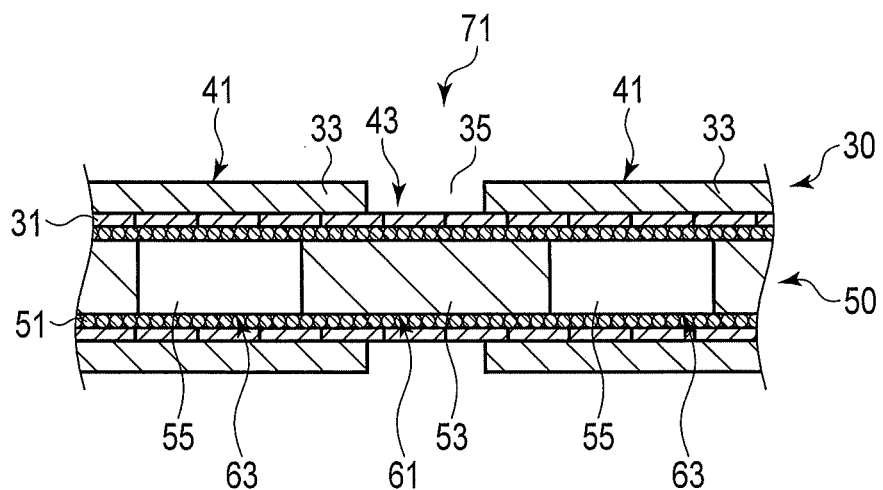
FIG. 3B is a diagram showing that the joint of the variable stiffness apparatus is in a high stiffness state.

Here, the first low bending stiffness portion 43 is sandwiched between the two first high bending stiffness portions 41 in the longitudinal axis direction of the first longitudinal member 30. As shown in FIGS. 3A and 3B, the first low bending stiffness portion 43 functions as a joint 71 of the variable stiffness apparatus 20 when one first high bending stiffness portion 41 is bent relative to the other first high bending stiffness portion 41. In FIGS. 3A and 3B, the moving mechanism 80 and the control device 90 are omitted for clarification of the illustration. FIG. 3A shows an initial state (first state), and the joint 71 is in a low stiffness state. Therefore, the joint 71 is easily bent by an external force. When the first low bending stiffness portion 43 overlaps the second high bending stiffness portion 61 as shown in FIG. 3B, the joint 71 is switched from the low stiffness state to the high stiffness state. Accordingly, when the joint 71 is in the high stiffness state, one first high bending stiffness portion 41 is difficult to bend with respect to the other first high bending stiffness portion 41 as compared with the case where the joint 71 in the low stiffness state, and maintains an approximately linear state. That is, the variable stiffness apparatus 20 and the flexible member 101 are difficult to bend and maintain an approximately linear state.

If the switch 103a in the control section 103 is turned off, the control device 90 controls the moving mechanism 80 so that the positional state switches from the second state to the first state.

As shown in FIG. 1A, the moving mechanism 80 moves the second longitudinal member 50 relative to the first longitudinal member 30, so that the positional state switches from the second state to the first state. At this time, the second high bending stiffness portion 61 overlaps the first high bending stiffness portion 41 over the entire length of the second high bending stiffness portion 61, and the first low bending stiffness portion 43 overlaps the second low bending stiffness portion 63 over the entire length of the first low bending stiffness portion 43. The variable stiffness apparatus 20 takes a low stiffness state in the first low bending stiffness portion 43. That is, the stiffness of the variable stiffness apparatus 20 partially decreases in the longitudinal axis direction of the variable stiffness apparatus 20.

The first space 35 (first low bending stiffness portion 43) is positioned and fixed relative to the desired area of the flexible member 101. Thus, by the second low bending stiffness portion 63 overlapping the first low bending stiffness portion 43, relatively low stiffness is provided to the desired area to which the first low bending stiffness portion 43 is fixed, which leads to decrease in stiffness of the desired area. That is, the stiffness decreases in part of the flexible member 101 where the first low bending stiffness portion 43 that the second low bending stiffness portion 63 overlaps is arranged. In other words, the variable stiffness apparatus 20 provides low stiffness to only part of the flexible member 101 in the entire length of the flexible member 101. Therefore, the flexible member 101 does not switch from the high stiffness state to the low stiffness state over the entire length of the flexible member 101, but partially switches from the high stiffness state to the low stiffness state. In other words, part of the total length of the flexible member 101 switches from the high stiffness state to the low stiffness state. Thus, the variable stiffness apparatus 20 varies the stiffness state of the variable stiffness apparatus 20 on the periphery of the first low bending stiffness portion 43, which results in a variation in the stiffness of the desired area in the flexible member 101.

Part of the flexible member 101 in the low stiffness state is easily deformed in accordance with the external force acting on the flexible member 101. Therefore, the flexible member 101 can be easily bent by an external force. When the joint 71 is in the low stiffness state, one first high bending stiffness portion 41 is more easily bent relative to the other first high bending stiffness portion 41 as compared with the joint 71 in the high stiffness state. That is, the variable stiffness apparatus 20 and the flexible member 101 are more easily bent.

By switching the positional state between the first state and the second state by the moving mechanism 80 in this manner, the stiffness of the desired area in the flexible member 101 is switched.

In the present embodiment, the second longitudinal member 50 is moved relative to the first longitudinal member 30, and the movement leads to variation in the stiffness of part of the variable stiffness apparatus 20 in the longitudinal axis direction of the variable stiffness apparatus 20. Specifically, the stiffness of part of the variable stiffness apparatus 20 on the periphery of the first low bending stiffness portion 43 is varied by the second high bending stiffness portion 61 and the second low bending stiffness portion 63. In the present embodiment, the variation in the stiffness of the part can vary the stiffness of the desired area in the flexible member 101, and can partially vary the stiffness state of the flexible member 101. In the embodiment, the combination of the first longitudinal member 30 and the second longitudinal member 50, and the arrangement of the core member 31, the first rigid members 33, the first high bending stiffness portions 41, the first low bending stiffness portions 43, the soft member 51, the second rigid members 53, the second high bending stiffness portions 61, and the second low bending stiffness portions 63 allow the configuration of the variable stiffness apparatus 20 to be simple and thin. This enables the flexible member 101 to be made thin. As described above, in the present embodiment, it is possible to provide the variable stiffness apparatus 20 that can easily adopt the configuration in which the flexible member 101 does not easily become thick.

In the present embodiment, the moving mechanism 80 moves the second longitudinal member 50 relative to the first longitudinal member 30. Therefore, in the present embodiment, the positional state can be quickly switched between the first state and the second state, which can improve the responsiveness of switching of the stiffness state of the flexible member 101.

Here, it is assumed that, unlike the present embodiment, the variable stiffness apparatus 20 varies the stiffness of a desired area in the flexible member 101 by using a shape memory member including, for example, a shape memory alloy. In this case, the variable stiffness apparatus 20 includes wirings (not shown) supplying an electric current, and inducing members (not shown) configured to generate heat upon receiving the electric current supplied from the wirings to transfer the generated heat to the shape memory member. The wirings are arranged in respective inducing members, and the inducing members are arranged apart from each other. The phase of the shape memory member may transition from a first phase to a second phase by heat transmitted from the inducing members. When the shape memory member is in the first phase, the shape memory member takes a low stiffness state. When the shape memory member is in the second phase, the shape memory member takes a high stiffness state having higher stiffness than in the low stiffness state. The variable stiffness apparatus 20 provides low stiffness to the flexible member 101 by the shape memory member in the low stiffness state, and provides high stiffness to the flexible member 101 by the shape memory member in the high stiffness state. Thereby, the variable stiffness apparatus 20 varies the stiffness of a desired area in the flexible member 101. The heated shape memory member in the high stiffness state returns to the low stiffness state by natural cooling. Herein, a state in which the flexible member 101 is provided with a relatively low stiffness by naturally cooling the shape memory member in the high stiffness state is referred to as a naturally-provided state. In the naturally-provided state, it takes time until the heat drops to the temperature in the low stiffness state. However, in the present embodiment, the variable stiffness apparatus 20 can provide the flexible member 101 with relatively low stiffness more quickly than in the naturally-provided state by the movement of the second longitudinal member 50. That is, in the present embodiment, the flexible member 101 can be switched from the high stiffness state to the low stiffness state in a shorter time than natural cooling. Further, since the wirings are arranged in the respective inducing members, it may be that the arrangement of the wirings is complicated, which complicates the configuration of the variable stiffness apparatus 20, causing the flexible member 101 to be thick. In the embodiment, however, the moving mechanism 80, and the arrangement of the core member 31, the first rigid members 33, the first high bending stiffness portions 41, the first low bending stiffness portions 43, the soft member 51, the second rigid members 53, the second high bending stiffness portions 61, and the second low bending stiffness portions 63 allow the configuration of the variable stiffness apparatus 20 to be simple and thin. This enables the flexible member 101 to be made thin.

In the present embodiment, the soft member 51 is shared by the second high bending stiffness portions 61 and the second low bending stiffness portions 63. Therefore, in the present embodiment, the number of components of the second longitudinal member 50 can be reduced, which enables the configuration of the variable stiffness apparatus 20 to be simple and thin, so as to allow the flexible member 101 to be thin.

In the present embodiment, the tubular soft member 51 can prevent abrasion of each of the core member 31 and the second rigid members 53 caused by the movement.

In the present embodiment, if the soft member 51 has a twisted wire sleeve, the mechanical strength of the soft member 51 is improved. Thereby, even if the moving mechanism 80 pulls or pushes the second longitudinal member 50, breakage of the soft member 51 due to the pulling or pushing can be prevented. In the present embodiment, if the soft member 51 has the contact coil, the bending stiffness of the soft member 51 is reduced. Thereby, the flexible member 101 can be provided with lower stiffness. In the present embodiment, the stiffness provided to the flexible member 101 can be adjusted by adjusting the density of the metal wires in the twisted wire sleeve, the diameter of the metal wires, the number of turns of the contact coil, the diameter of the wire of the contact coil, and the elasticity of the contact coil.

In the present embodiment, by the soft member 51, the second rigid member 53 can be easily positioned, and the length of the second space 55 can be easily specified. In the present embodiment, by the soft member 51, the second high bending stiffness portion 61 and the second low bending stiffness portion 63 can be easily positioned, and the length of each of the second high bending stiffness portion 61 and the second low bending stiffness portion 63 can be easily specified. In the present embodiment, the mechanical strength of the second longitudinal member 50 can be improved by the soft member 51.

Here, it is assumed that, unlike the present embodiment, the soft member 51 is omitted, a small-diameter connecting member is arranged in the second space 55, and the second rigid member 53 is, for example, a solid large-diameter portion. Assume that ends of the connecting member are fixed to the second rigid members 53 adjacent to the ends. Assume that, when the flexible member 101 is in a bending state, the positional state is switched from the first state to the second state, and the second longitudinal member 50 moves relative to the first longitudinal member 30. At this time, the pulling force of the moving mechanism 80 pulling the second longitudinal member 50 may increase due to the connections between the connecting member and the second rigid members 53 and the bending state. Then, stress may be concentrated on a connection portion of the connecting member and the second rigid member 53, which may lead to fracture of the connecting portion. If the connecting member is integral with the second rigid member 53, the strength of a connection portion may be insufficient, so that the second longitudinal member 50 may easily break. If the connecting member is a wire with a small diameter and the second rigid member 53 is a metal pipe, the assembly of the second longitudinal member 50, such as the connection of the connecting member and the second rigid member 53, may not be easy.

However, in the present embodiment, the soft member 51 is arranged, the second rigid members 53 are arranged at desired intervals from each other inside the flexible member 51, and the second space 55 is arranged. Thereby, in the present embodiment, even if the pulling force of the moving mechanism 80 is increased in a state where the flexible member 101 is bent, the concentration of stress can be avoided, breakage of the connecting portion can be avoided, and easy breakage of the second longitudinal member 50 associated with lack of strength of the connecting portion can be avoided. In the present embodiment, the second longitudinal member 50 can be easily assembled. Further, in the present embodiment, since no member is arranged in the second space 55, the number of components of the second longitudinal member 50 can be reduced.

In the present embodiment, the core member 31 is shared by the first high bending stiffness portions 41 and the first low bending stiffness portions 43. Therefore, in the present embodiment, the number of components of the first longitudinal member 30 can be reduced, which enables the configuration of the variable stiffness apparatus 20 to be simple and thin, so as to allow the flexible member 101 to be thin.

In the present embodiment, by the core member 31, the first rigid member 33 can be easily positioned, and the length of the first space 35 can be easily specified. In the present embodiment, by the core member 31, the first high bending stiffness portion 41 and the first low bending stiffness portion 43 can be easily positioned, and the length of each of the first high bending stiffness portion 41 and the first low bending stiffness portion 43 can be easily specified. In the present embodiment, the core member 31 enables easy assembling of the first longitudinal member 30. In the present embodiment, the core member 31 enables improvement of the mechanical strength of the first longitudinal member 30.

In addition to the switching of the stiffness, under a condition where an external force other than gravity is exerted on the flexible member 101, the variable stiffness apparatus 20 also functions as a bidirectional actuator configured to switch the shape of the flexible member 101. Under a condition where no external force other than gravity is exerted on the flexible member 101 and the variable stiffness apparatus 20 is in the second state, the variable stiffness apparatus 20 also functions as a single-direction actuator configured to restore the shape of the flexible member 101 to the original shape.

For example, various members (not shown) are arranged in a space that is inside the flexible member 101 and outside the first longitudinal member 30. The members include, for example, a light guide member (not shown) such as an optical fiber. The light guide member guides illumination light to the distal end portion of the flexible member 101 in order to emit the illumination light from the distal end portion of the flexible member 101 to the outside of the endoscope 100, for example. In the present embodiment, the second longitudinal member 50 moves, and the first longitudinal member 30 is arranged between the second longitudinal member 50 and a light guide member (not shown). Therefore, the first longitudinal member 30 can prevent the abrasion of each of the second longitudinal member 50 and the light guide member caused by the movement of the second longitudinal member 50.

In the present embodiment, the first longitudinal member 30 is positioned and fixed relative to the flexible member 101, and the second longitudinal member 50 is moved by the moving mechanism 80. However, the configuration does not need be limited thereto. Only either one of the first longitudinal member 30 and the second longitudinal member 50 has to be moved by the moving mechanism 80.

[Modification]

Figure 4:
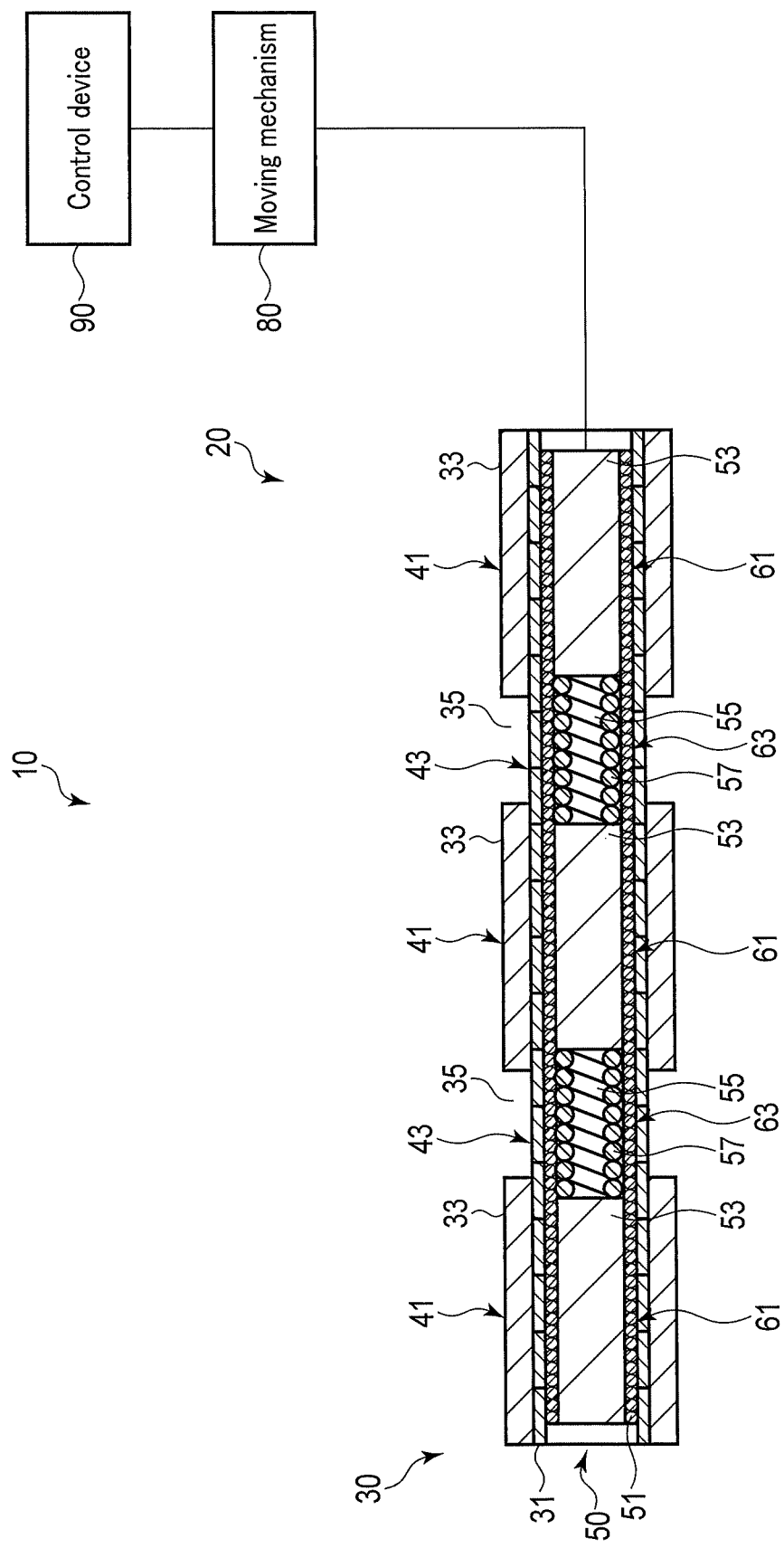
FIG. 4 is a diagram showing a modification of a second longitudinal member.

A modification of the second longitudinal member 50 will be described with reference to FIG. 4. Since a first longitudinal member 30 in this modification is the same as the first longitudinal member 30 of the present embodiment, the explanation thereof is omitted.

A second longitudinal member 50 includes internally-soft members 57 arranged inside a soft member 51. The internally-soft members 57 are arranged in the second spaces 55, respectively. In the present embodiment, two internally-soft members 57 are arranged. The second rigid members 53 and the internally-soft members 57 are alternately arranged inside the soft member 51 in the longitudinal axis direction of the second longitudinal member 50. Thus, the internally-soft member 57 is arranged between two second rigid members 53. Ends of the internally-soft member 57 are in contact with the second rigid member 53 adjacent to the ends. The ends of the internally-soft member 57 may be fixed to the second rigid members 53 adjacent to the ends by, for example, bonding or welding. The outer peripheral surface of the internally-soft member 57 is in contact with the inner peripheral surface of the soft member 51. Note that the outer peripheral surface of the internally-soft member 57 may be spaced apart from the soft member 51. The internally-soft members 57 are positioned on the soft member 51 so that the internally-soft members 57 are arranged inside the soft member 51. The internally-soft members 57 are arranged in order to define the intervals between the second rigid members 53 (the second high bending stiffness portions 61), in other words, the length of the second low bending stiffness portions 63. The internally-soft members 57 arranged between the second rigid members 53 are arranged for positioning the second rigid members 53.

The internally-soft member 57 has, for example, a spring member. The spring member has, for example, a tightly-wound spring. The spring member may have, for example, a loosely-wound spring. The internally-soft member 57 may have, for example, a linear member such as a thin wire, or an elastic member such as rubber. The outer diameter of the winding of the internally-soft member 57 is about the same as the outer diameter of the second rigid member 53.

The second low bending stiffness portion 63 further includes an internally-soft member 57 covered with part of the soft member 51.

In this modification, by the internally-soft member 57, enables easy positioning of the second rigid members 53 (the second high bending stiffness portions 61), which leads to easy assembling of the second longitudinal member 50.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   a flexible member; and
   a variable stiffness apparatus disposed in the flexible member, the variable stiffness apparatus comprising:
      a first longitudinal member; and
      a second longitudinal member movable relative to the first longitudinal member,
      the first longitudinal member including a core member covering an outer periphery of the second longitudinal member;
      the second longitudinal member including a soft member covered by the core member,
      the first longitudinal member further including at least one first high bending stiffness portion covering one or more portions of the core member, and at least one first low bending stiffness portion comprising a part of the core member that is not covered with the first high bending stiffness portion, the first low bending stiffness portion having a lower bending stiffness than a bending stiffness of the first high bending stiffness portion,
      the second longitudinal member further including at least one second high bending stiffness portion and at least one second low bending stiffness portion having a lower bending stiffness than a bending stiffness of the second high bending stiffness portion,
      wherein a stiffness of part of the variable stiffness apparatus is configured to be varied by changing a relative position of the first longitudinal member and the second longitudinal member.

2. The endoscope according to claim 1, further comprising a moving mechanism configured to move the second longitudinal member relative to the first longitudinal member.

3. The endoscope according to claim 2, wherein, by moving the second longitudinal member, the variable stiffness apparatus switches a positional state of the second longitudinal member relative to the first longitudinal member between a first state to provide the flexible member with first stiffness and a second state to provide the flexible member with second stiffness higher than the first stiffness.

4. The endoscope according to claim 3, wherein,
in the first state, the second low bending stiffness portion is arranged on the periphery of the first low bending stiffness portion, and,
in the second state, the second high bending stiffness portion is arranged on the periphery of the first low bending stiffness portion.

5. The endoscope according to claim 4, wherein,
in the first state, the second high bending stiffness portion is arranged on a periphery of the first high bending stiffness portion, and,
in the second state, the second low bending stiffness portion is arranged on the periphery of the first high bending stiffness portion.

6. The endoscope according to claim 1, wherein the soft member is tubular.

7. The endoscope according to claim 6, wherein the soft member includes a metal member.

8. The endoscope according to claim 7, wherein the soft member comprises a twisted wire sleeve in which metal wires are twisted with each other.

9. The endo scope according to claim 7, wherein the soft member comprises a contact coil.

10. The endoscope according to claim 1, wherein
the first high bending stiffness portion includes a tubular first rigid member covering the core member.

11. The endoscope according to claim 10, wherein the first high bending stiffness portion further includes part of the core member that is covered with the first rigid member.

12. The endoscope according to claim 1, wherein the first high bending stiffness portion and the first low bending stiffness portion are alternately arranged in a longitudinal axis direction of the first longitudinal member.

13. The endoscope according to claim 1, wherein
the soft member is tubular, and
the second high bending stiffness portion includes a second rigid member arranged inside the soft member.

14. The endoscope according to claim 13, wherein the second high bending stiffness portion further includes part of the soft member covering the second rigid member.

15. The endoscope according to claim 13, wherein the second low bending stiffness portion includes part of the soft member covering an inner space of the soft member where the second rigid member is not arranged.

16. The endoscope according to claim 13, wherein the second low bending stiffness portion includes an internally-soft member covered with part of the soft member.

17. The endoscope according to claim 1, wherein the second high bending stiffness portion and the second low bending stiffness portion are alternately arranged in a longitudinal axis direction of the second longitudinal member.

18. A stiffness varying method of varying a stiffness of a part of a variable stiffness apparatus disposed in a flexible member included in an endoscope, wherein the variable stiffness apparatus comprising: a first longitudinal member; and a second longitudinal member movable relative to the first longitudinal member, the first longitudinal member including a core member covering an outer periphery of the second longitudinal member; the second longitudinal member including a soft member covered by the core member, the first longitudinal member further including at least one first high bending stiffness portion covering one or more portions of the core member, and at least one first low bending stiffness portion comprising a part of the core member that is not covered with the first high bending stiffness portion, the first low bending stiffness portion having a lower bending stiffness than a bending stiffness of the first high bending stiffness portion, and the second longitudinal member further including at least one second high bending stiffness portion and at least one second low bending stiffness portion having a lower bending stiffness than a bending stiffness of the second high bending stiffness portion, the method comprising:
varying the stiffness of the part of the variable stiffness apparatus by changing a relative position of the first longitudinal member and the second longitudinal member.

* * * * *